US007813011B2

(12) United States Patent
Yan

(10) Patent No.: US 7,813,011 B2
(45) Date of Patent: Oct. 12, 2010

(54) METHOD OF CONVERSION OF A HARD-COPY DOCUMENT CONTAINING TEXT OR IMAGE DATA INTO THE ELECTRONIC DOCUMENT

(75) Inventor: David Yan, Moscow (RU)

(73) Assignee: ABBYY Software Ltd, Nicosia (CY)

( * ) Notice: Subject to any disclaimer, the term of this patent is extended or adjusted under 35 U.S.C. 154(b) by 1002 days.

(21) Appl. No.: 11/558,914

(22) Filed: Nov. 12, 2006

(65) Prior Publication Data

US 2007/0091385 A1   Apr. 26, 2007

Related U.S. Application Data

(63) Continuation-in-part of application No. 11/456,092, filed on Jul. 7, 2006.

(51) Int. Cl.
*H04N 1/04* (2006.01)
(52) U.S. Cl. .................. 358/474; 358/496; 358/498; 358/443
(58) Field of Classification Search .......... 358/474, 358/496, 498, 443, 408, 505, 471, 401, 501; 382/312, 318, 319
See application file for complete search history.

(56) References Cited

U.S. PATENT DOCUMENTS

| 4,694,259 | A | * | 9/1987 | Carickhoff et al. | 331/1 A |
|---|---|---|---|---|---|
| 5,377,022 | A | * | 12/1994 | Street et al. | 358/498 |
| 5,386,446 | A | * | 1/1995 | Fujimoto et al. | 378/20 |
| 6,075,622 | A | * | 6/2000 | Hadgis et al. | 358/474 |
| 6,236,831 | B1 | * | 5/2001 | Mei et al. | 399/411 |
| 6,606,091 | B2 | * | 8/2003 | Liang et al. | 345/424 |
| 6,760,132 | B1 | * | 7/2004 | Shibata | 358/488 |
| 6,940,664 | B1 | * | 9/2005 | Pilu | 359/806 |

* cited by examiner

*Primary Examiner*—Houshang Safaipour
(74) *Attorney, Agent, or Firm*—Hahn & Moodley LLP; Vani Moodley, Esq.

(57) ABSTRACT

A method of obtaining graphical information from a single- or multi-page document printed on a hard media where reading out of the position of the document elements is performed by using a method of volumetric scanning of a document (even closed) is described. Processing of scanning results, comprises joining up the separate scanning layers scanning results, removing noise, correction of document image orientation, dividing information into portions relating to separate pages, is performed after reading the information. Then text information recognition contained in the graphical file is performed. Information may be read out by using methods of magnetic resonance scanning, supersonic scanning, X-ray scanning etc. The results of scanning in electronic form may be stored for further transmission thereof on a medium or via communication channels to a distant location for recognition.

8 Claims, 2 Drawing Sheets

METHOD OF CONVERSION OF A HARD-COPY DOCUMENT CONTAINING TEXT OR IMAGE DATA INTO THE ELECTRONIC DOCUMENT

PATENT CASE TEXT

This application is a continuation-in-part, of application Ser. No. 11/456,092, filed Jul. 7, 2006, U.S.

DESCRIPTION

The present invention relates generally to the area of document type conversion and particularly to printed hard-copy documents conversion with text or image data either single- or multi-page into electronic form via scanning of the initial document.

PRIOR ART

Methods and devices for scanning of documents capable of scanning single pages or lists of a document by means of radiating its surface, on which text is printed or embossed, by visible or other radiation (electromagnetic or other) and picking up the echoed signal are known in the art. Radiation types which do not penetrate into carrier material and print material and well reflected from the carrier material are used. Use of such scanners is based on the different intensity of the signal reflected from the carrier surface and the signal reflected from the surface of an embossed image (glyph).

Such devices comprise well-known optical scanners for inputting images into a computer (for example, U.S. Pat. No. 4,677,494, Sue, Jun. 30, 1987).

Scanners for topographic scanning, applied, for example, for nondestructive checking of products or for medical diagnostics, are known in the art (for example, U.S. Pat. No. 5,386,446, Fujimoto, et al., Jan. 31, 1995). Radiation types penetrating to some extent into the carrier material and print material and reflected from their surfaces to a variable degree are used. Use of such scanners is based on the different intensity of the signal reflected from the division surface between the materials which have different properties.

The known methods and devices for scanning allow processing one page at a time (one-sided scanning) or one list at a time (double-sided, or duplex, scanning). The document sustains a considerable mechanical impact. Some document types, for example, old books, do not allow scanning without special treatment, such as mechanical division into pages. This may cause the loss of information as well as damage to a valuable book.

This shortcoming of the known methods and devices confines greatly the ability of using thereof for data reading out from multi-page documents.

SUMMARY OF THE INVENTION

The declared technical result is achieved by using a scanning method in which radiation type is chosen depending on the physical properties of the document's media matter and the printer's ink matter, so that the chosen radiation has different reflectivity and/or refractivity therein.

The proposed method comprises the scanning of single- or multi-page hard copy documents by using a method of volumetric scanning of printed or embossed information.

BRIEF DESCRIPTION OF THE DRAWINGS

The essence of the invention is illustrated by the FIGS. 1, 2 and 3.

FIG. 1 represents the result of the volumetric scanning of multi-page document (the example comprises 3 sheets document). For the better representation the text referring to different pages is shown by the font of different thickness.

FIG. 2 and FIG. 3 shows a device as a preferred embodiment for the volumetric scanning in a simplified form and an initial document placing therein.

DETAILED DESCRIPTION OF THE INVENTION

Figure 1:
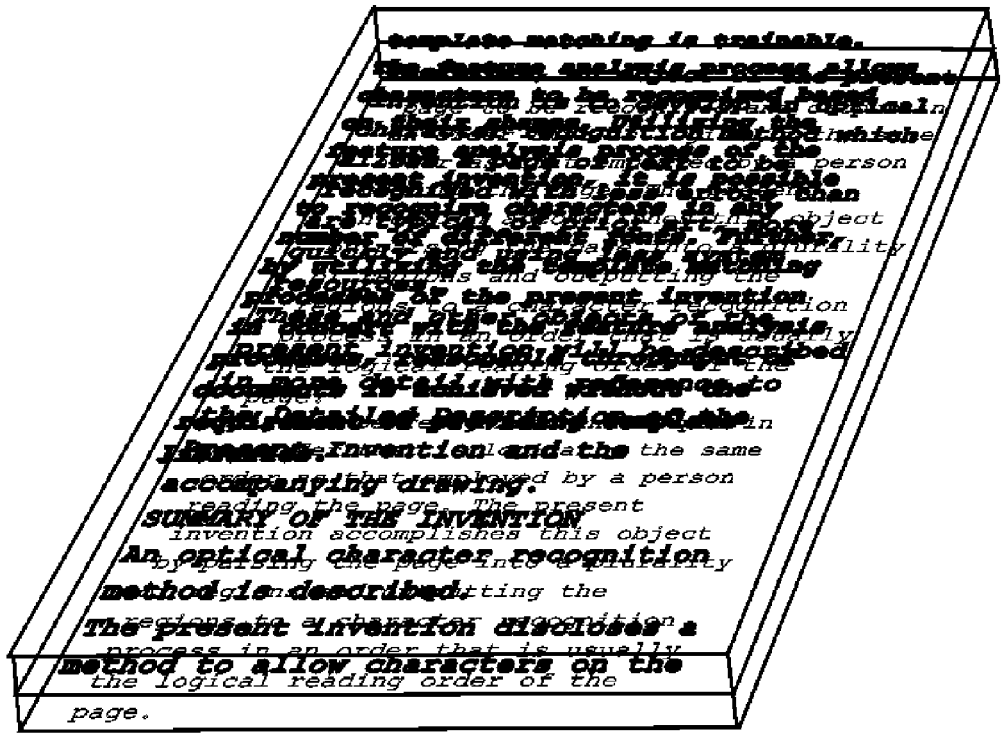
FIG. 1 An approximate embodiment of a multi-page document, obtained with by using the proposed invention.

The arbitrary spatially oriented document 1 is placed into the scanning means operating area 3, for example, feeding by conveyer 2.

The layer-by-layer scanning is performed with each layer scanning results storage.

On obtaining the whole set of layers data, the results are combined, all the irrelevant data (noise incl.) is eliminated, and the electronic document orientation is adjusted to that suitable for the further processing.

After that the graphical data referring to each document page is singled out (extracted).

The graphical data presumably containing text is directed for recognition by one of the known means.

The recognition results may be then saved.

The volumetric scanning means 3 is connected to a single layers scanning results combining means 4, further connected to an irrelevant data elimination (clearing) means, further connected to spatial orientation adjustment means 6. Further a means for the text recognition 7 from the graphical file may be connected. Said means device for the text recognition from the graphical file may be located distantly. In this case all stored data is transferred distantly to the place of further processing (incl. recognition) by any of the known and commonly used means: by physical media, via internet or by other communication channels.

The mentioned devices may be realized either as separate devices or electronic blocks, or may be joined into groups or in the entire joint block (module).

The data processing means (5) (scanning results combination, data preliminary processing and data recognition) may be realized on the base of one or more data processing means on the base of computer. Moreover, to the abovementioned devices may be provided with data storage means, either text and/or graphic, on the base of the same or the different device.

Depending on the data media matter, data image matter, required resolution, other parameters, the volumetric scanning means used should be based on the nuclear-magnetic resonance, ultra-sonic, X-ray, X-ray tomography or other principles.

The volumetric scanning means is chosen so that its effecting radiation (or the other effecting factor) has different altering ability (on echoing or passing, on reflecting or refracting etc.) hitting the data media matter and data image (printer's ink) matter.

In a case the document is formed by the media matter local volume or shape altering, the difference in the reflecting or refracting ability appears due to local altering of the media matter density and/or presence of local hollows in the matter or between the document paper sheets.

The volumetric scanning means resolution is chosen to be sufficient for reliable recognition of all image constituents (elements) on the data media.

The thickness of the single scanned layer should be not more then the document single sheet.

In the volumetric scanning the multi-page document is assumed as a three-dimensional object, and the required technical result is obtained by the addition (introduction) of supplementary operations, performed by a computer (single layers combination, single pages data extraction, etc.)

Figure 2:
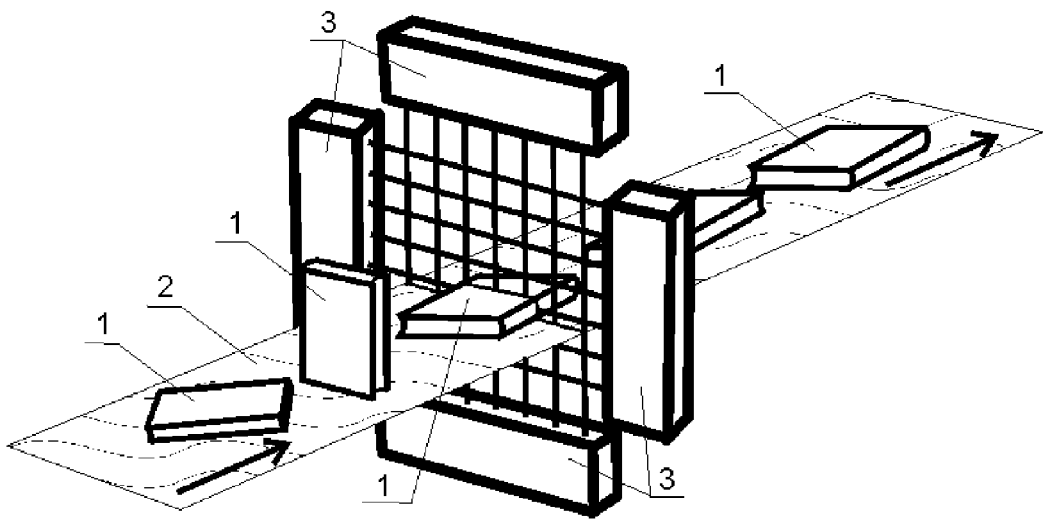
FIG. 2 Scanning of multi-page documents moving on a conveyer.
Figure 3:
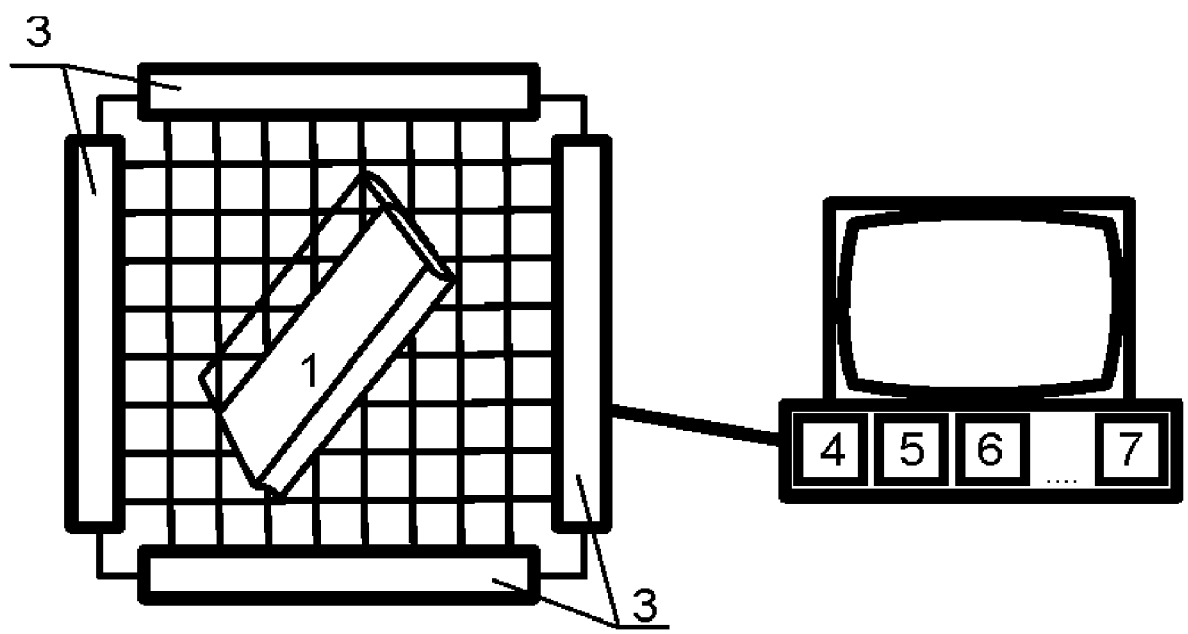
FIG. 3 The main means as a preferred embodiment illustrating the proposed method.

The essence of the suggestion is illustrated in FIGS. 1-3.

The results of multi-page document processing (a three-page document is used as an example) are shown in FIG. 1. Text in FIG. 1 has different thickness only for greater obviousness and ability to attribute text to its corresponding page. The present results look like a text array printed in a font whose thickness is the same as in the original document.

The essence of the suggestion is illustrated in FIGS. 2 and 3.

A single- or multi-page document (1) arbitrarily oriented in space is placed in a scanning region (3), for example, by a document feeder that uses a conveyer (3). The layer-by-layer scanning is performed and the results of scanning are saved for each layer. Once information about the whole set of layers is obtained, the data about the layers are merged (4), extraneous information (noise) is erased, and orientation convenient for further processing is set (6). Graphical information which presumably contains text is then sent for recognition (7) by one of the known methods. The results of recognition may be further saved.

Results of volumetric scanning, after they are obtained from a scanner or after preliminary processing (5) such as integration of scanning results, may be transmitted, on carriers or via communication channels or by another way, to a place where preliminary processing, recognition, systematization, and other operations are performed. Said place may be located at a distance from the place of scanning.

Operations of scanning and further processing of information (including saving) may also be separate in time.

Depending on the material of a document, material used for printing, required resolution capacity, and other factors, a nuclear magnetic resonance (NMR), supersonic or X-ray (X-ray tomography) volumetric scanning means or other known tools are applied

What is claimed is:

1. A method of converting a hard-copy document into electronic form via scanning, the method being performed by a scanner, the method comprising:
    performing a volumetric scan of the hard-copy document comprising:
        performing radiation treatment of the hard-copy document with a at least one of a printed, volumetric-formed, and embossed text;
        receiving signals as a result of the radiation treatment;
        combining the received signals;
        rendering an electronic document based on the combining of the received signals; and
        sending the electronic document to at least one of a character and text recognition, wherein performing radiation treatment comprises use of radiation of different reflecting or refracting ability based on at least one of a medium matter, volumetric-formed letters matter and matter of any printed letters thereon, and said volumetric scan is performed on a layer by layer basis.

2. The method as recited in claim 1, where combining the received signals is performed via consolidation of signals obtained from scanning of layers.

3. The method as recited in claims 1, where said rendering the electronic document, further comprising removing noise; document image orientation adjustment if necessary; division of electronic document information into parts relating to single pages of the initial document.

4. The method as recited in claim 1, where said volumetric scanning is performed at the resolution sufficient for reliable distinguishing of information signs on said medium and said single layers are assigned to be not thicker then the single medium sheet being scanned.

5. The method as recited in claim 1, where the data scanning is performed with the use of nuclear-magnetic resonance means.

6. The method as recited in claim 1, where the data scanning is performed with the use of ultra sonic means.

7. The method as recited in claim 1 where the scanning is performed with the use of X-ray means.

8. The method as recited in claim 3, where the electronic document is stored in memory and further transmitted distantly for recognition to a geographically different place.

\* \* \* \* \*